United States Patent [19]
Weber et al.

[11] Patent Number: 4,778,449
[45] Date of Patent: Oct. 18, 1988

[54] MONITORING SYSTEM FOR THE REMOTE SUPERVISION OF A PLURALITY OF GRAVITY PERFUSION SETS

[75] Inventors: Jean-luc Weber, Salon de Provence; Sylviane M. M. Confort, wife Gouny, Marseille, both of France

[73] Assignee: Bertin & Cie, Plaisir Cedex, France

[21] Appl. No.: 9,525

[22] Filed: Feb. 2, 1987

[30] Foreign Application Priority Data

Feb. 3, 1986 [FR] France ............... 86 01438

[51] Int. Cl.$^4$ ............................................. A61M 5/00
[52] U.S. Cl. .................................... 604/65; 128/903; 128/DIG. 13
[58] Field of Search ................. 604/65, 66, 67, 80, 604/81, 253; 128/DIG. 12, DIG. 13, 903

[56] References Cited

U.S. PATENT DOCUMENTS

| | | |
|---|---|---|
| 4,051,522 | 9/1977 | Healy et al. ............... 128/903 X |
| 4,261,360 | 4/1981 | Perez .................... 128/DIG. 13 |
| 4,534,756 | 8/1985 | Nelson .................... 604/65 X |
| 4,553,958 | 11/1985 | Le Cocq . |
| 4,600,401 | 7/1986 | Kamen ................... 604/65 |
| 4,619,653 | 10/1986 | Fischell ............... 128/DIG. 13 |
| 4,629,015 | 12/1986 | Fried et al. ............. 604/66 X |
| 4,650,465 | 3/1987 | Langer et al. ............ 604/65 |

*Primary Examiner*—Edward M. Coven
*Attorney, Agent, or Firm*—Watson, Cole, Grindle & Watson

[57] ABSTRACT

The supervision system comprises an electrical line for the transmission of digital data, at least one perfusion set including a flow meter and a module for encoding and for transmission in digital form on the line of the data concerning the instantaneous flowrate which are supplied by the flow meter, and a central unit for the processing of the said data, which central unit is connected to the said line by means of a decoding module. The central unit comprises at least one display screen, on which the quantities representing the condition of the perfusion set are displayed in analog and alphanumeric form. Application to the supervision of perfusions in a hospital environment.

13 Claims, 3 Drawing Sheets

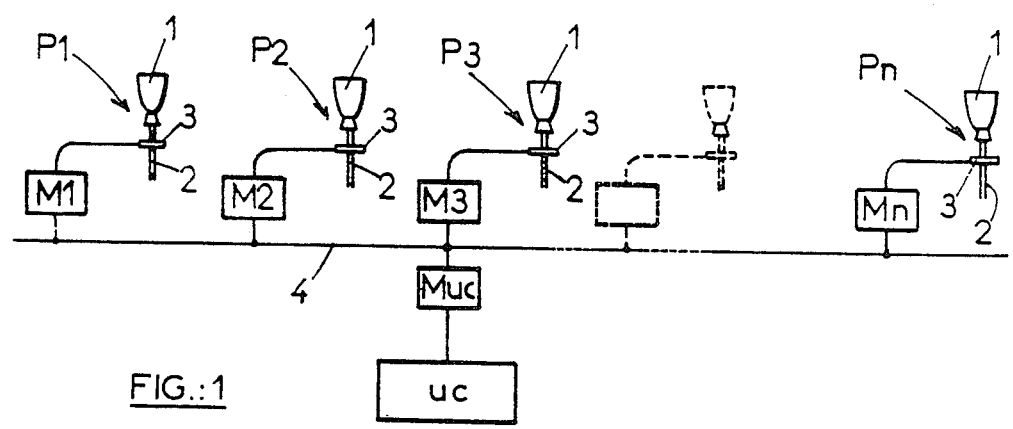
FIG.:1
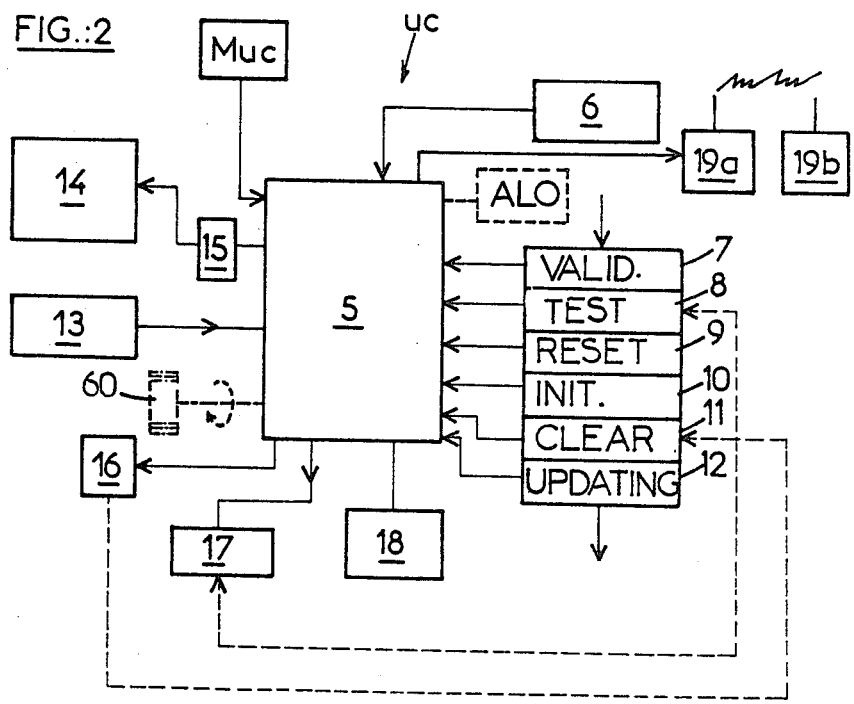
FIG.:2

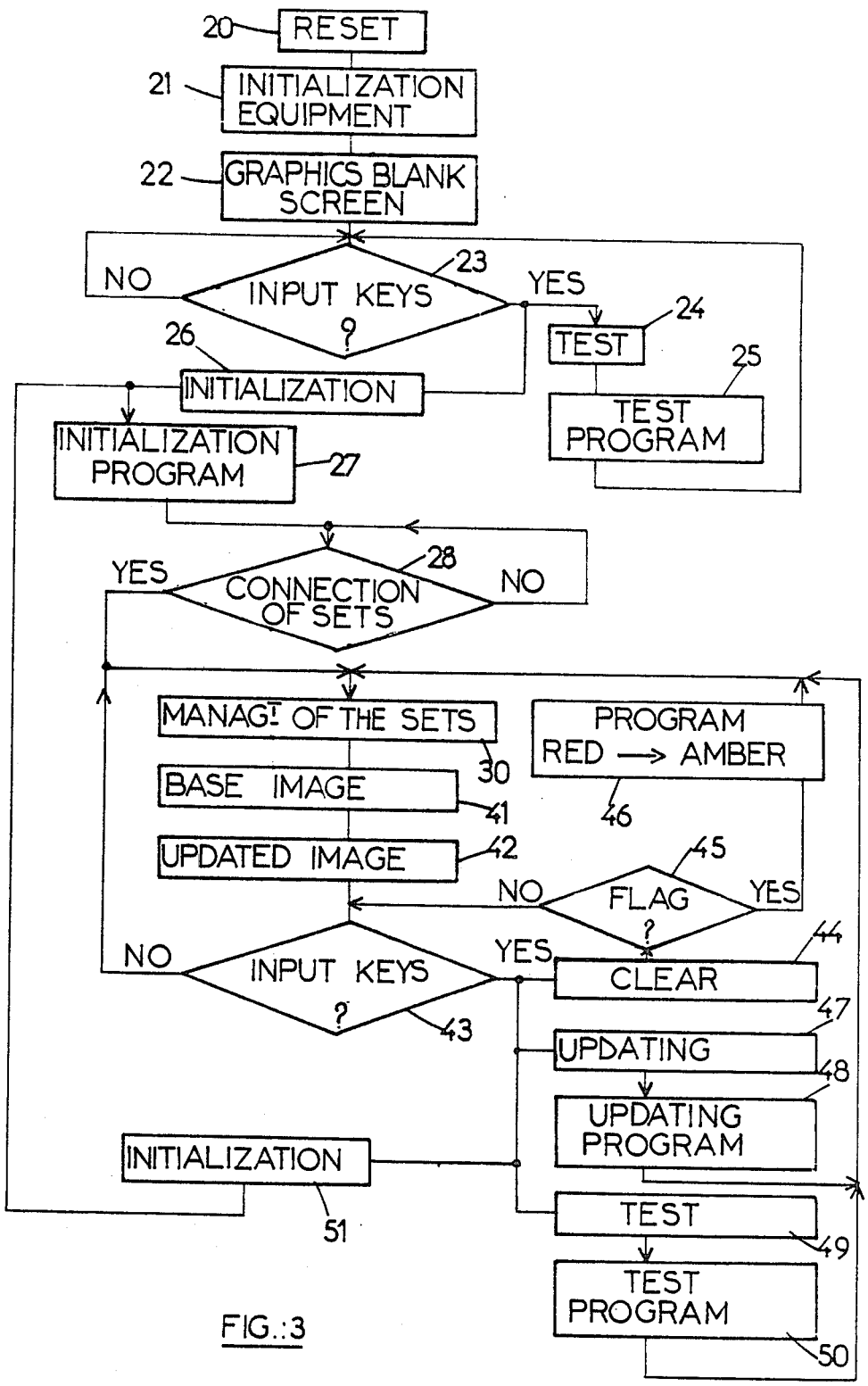
FIG.:3

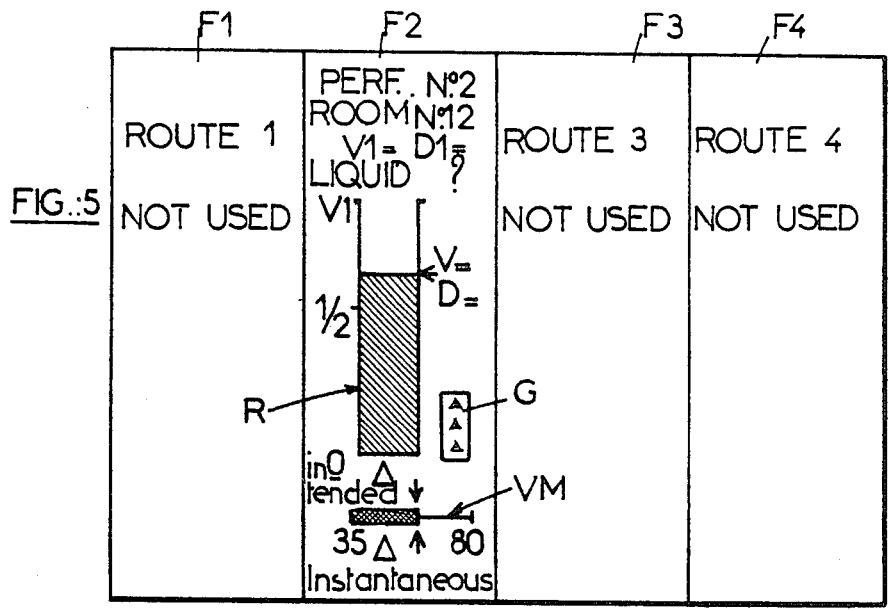
FIG.:5
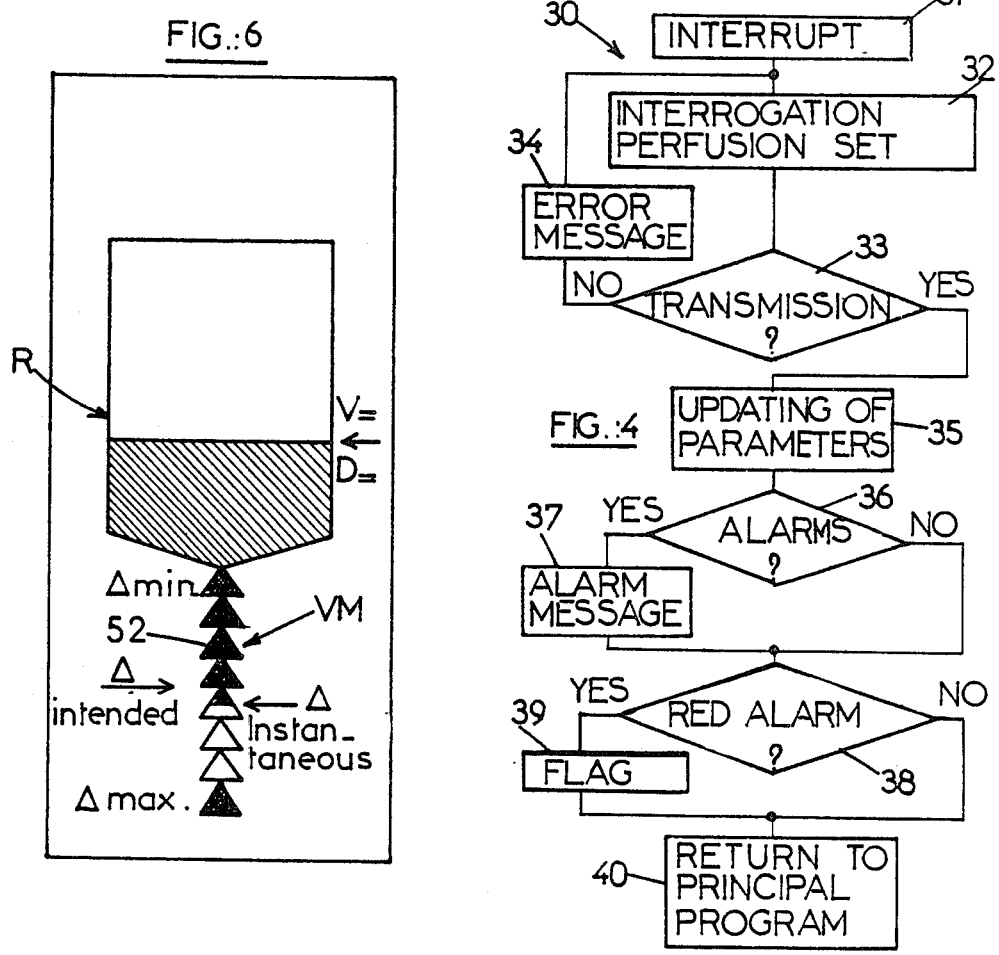
FIG.:6
FIG.:4

MONITORING SYSTEM FOR THE REMOTE SUPERVISION OF A PLURALITY OF GRAVITY PERFUSION SETS

The invention relates to a process and a system for the remote supervision of at least one perfusion set.

Various solutions are employed in a hospital environment to slowly inject liquids by the parenteral route, namely injection by means of an electrical syringe (power syringe), injection by means of a programmed perfusion pump and perfusion by gravity.

The first two techniques mentioned above rely on equipment situated in the patient's room, at the foot of the bed, permitting the assurance of a constant flow of the product to be injected with a high degree of accuracy in the order of 1/1,000 to 1/10,000. These apparatuses are utilized in the intensive care sector or in circumstances in which it appears necessary to completely monitor the flowrate of product supplied to the body. They require, in particular, venous catheterization in order to ensure complete permeability of the route. These items of equipment are certainly costly, and are used only in a limited number of cases.

For this reason, approximately 80% of the perfusions carried out in Europe rely on the technique of perfusion by gravity. This type of perfusion offers the advantage of low-cost equipment (bottles, tubes, needles) and convenient setting-up, at the expense, nevertheless, of proper control of the flow, which necessitates constant and attentive supervision and, in consequence, frequent visits by the responsible personnel to the patients undergoing perfusion.

The setting-up of the perfusion by gravity must be initialized by this responsible person, by empirically estimating a perfusion flowrate which will permit the patient to absorb the entire quantity of the perfusion during a period of time determined by the physician. This flowrate is generally corrected, in terms of addition or subtraction, by the responsible person, some tens of minutes after setting up the perfusion, in order to approach the optimal flowrate. Throughout the entire duration of the perfusion, the person responsible monitors whether the perfusion is proceeding correctly and checks that there is no circuit interruption which may possibly be caused by the patient.

The person responsible is generally instructed to supervise several perfusions and, in the large departments, several persons may be dedicated solely to the frequent visiting of the rooms of the patients undergoing perfusion.

The object of the invention is to provide a process and a system for remote supervision which permit a single responsible person to assess at any time, from a control room, the proper operation of one or more perfusion sets situated at different locations and permit this responsible person to be alerted within an adequate period of time in the event of an anomaly in the progress of the perfusion. A more specific object of the invention is to permit this responsible person to carry out permanent supervision, in real time, of the progress of the perfusion or perfusions which are in progress and for which he is responsible. Furthermore, although the invention is principally concerned with the supervision of sets for perfusion by gravity, it is not limited to this type of perfusion and may be applied likewise to the techniques of perfusion involving a controlled flowrate, in particular those mentioned above.

To this end, the subject of the invention is a process for the remote supervision of at least one perfusion set for the injection of a liquid into a patient, wherein:
  each perfusion set to be supervised is connected to a line for the transmission of digital data,
  there is allocated to each perfusion set to be supervised an identification code which is independent of its geographical location,
  the injection flowrate of liquid is measured at each set under supervision,
  this information is periodically sent to a central processing unit by the line for the transmission of digital data, and
  there are displayed on at least one monitoring screen an identification data item which is a function of the said code, as well as the instantaneous flowrate of liquid at each perfusion set under supervision.

According to another feature, the instantaneous flowrate is measured by counting the drops to be injected over short consecutive periods of approximately 1 minute, this is compared with the nominal flowrate initially intended, and the result of the said comparison is displayed.

A further subject of the invention is a system for the remote supervision of at least one perfusion set for the injection of a liquid into a patient, which system comprises an electrical line for the transmission of digital data, at least one perfusion set comprising a flow meter and a module for the encoding and the transmission in digital form, over the line, of the data concerning the instantaneous flowrate which are supplied by the flow meter, a central unit for the processing of the said data, which central unit is connected to the said line by means of a decoding module, and at least one monitoring screen for the display of identification and operating data of each perfusion set under supervision.

Preferably, the said electrical line is a general-purpose transmission line of the electrical power distribution network.

Further features and advantages of the present invention will be evident from the description, which will follow, of an embodiment which is given solely by way of example and illustrated by the accompanying drawings, in which:

FIG. 1 is a simplified diagram of a system for the remote supervision of sets for perfusion by gravity;

FIG. 2 is a block diagram of the central unit of the system of FIG. 1;

FIG. 3 is an algorithm of the principal program executed by the central unit of FIG. 2;

FIG. 4 is an algorithm of a subprogram illustrating the management of the perfusion sets from the central unit;

FIG. 5 is a representation of a monitoring screen in the form in which it appears to a person responsible for the supervision of perfusions; and FIG. 6 shows a variant of the presentation of the data concerning the monitoring of perfusion in a window of the monitoring screen.

FIG. 1 shows, in diagrammatic form, a system for the supervision, with the use of a central unit UC, of a certain number of sets for perfusion by gravity P1, P2, P3, ... Pn. Each perfusion set includes a bottle 1 which is intended to be filled with the liquid to be injected into the patient and which, to this end, is connected by a tube 2 to a needle (not shown). On each tube 2 there is mounted a flow meter 3 which, in the described case of perfusion by gravity, is formed by a drop counter such as, for example, the IMED 730 apparatus of the company IMED, U.S.A. The flow meter 3 is possibly associated with a display device (not shown), which permits the reading of the number of drops per unit time directly at the location of the perfusion, in the customary manner. The flow meters 3 of the perfusion sets P1 to Pn are each connected to a module M1 to Mn respectively, which assures the encoding of the data concerning the number of drops per unit time supplied by the corresponding flow meter 3 and transmission thereof, in digital form, on an electrical transmission line 4. For its part, the central unit UC is connected to the transmission line 4 by means of a decoding module Muc. Each perfusion set P1 ... Pn has a serial number or identification code, which is specific to it and will be recognized by the central unit UC.

The electrical transmission line 4 may form part either of a specialized network for the transmission of data or of a direct current or alternating current eletrical power distribution network such as, for example, the domestic low-tension alternating current electrical power distribution network. The process for the transmission of digital data by means of such a transmission line and of the associated modules M1 to Mn and Muc is already known, and will not be described in detail. It will be possible, in particular, to refer to the patent application FR-A-2,558,667, which gives a detailed description of the transmission process, of the network and of the associated modules which may be utilized in the monitoring system according to the invention.

Reference will now be made to FIG. 2, which shows the various components of the central unit UC, which is organized around an electronic circuit 5, such as the circuit EFS-MPU 8, which utilizes the MC 68008 16-bit microprocessor of the company MOTOROLA. With the circuit 5 there are associated the decoding module Muc, a stop-start switch 6, a set of six luminous keys 7 to 12, the function of which will be explained herein below, a digital keyboard 13 for inputting the data, and a visual display screen 14 which is connected to the circuit 5 by means of a graphics management circuit 15 such as the circuit EFS-VIG-1 of the company THOMSON. The electronic circuit 5 also drives an audio alarm generator 16, which has a connection with the clear key 11 for activation thereof in the event of the occurrence of an alarm, as well as a display device 17, for example a liquid-crystal display device, which is connected to the test key 8 so as to display a control code or an error code on certain digits in the event of actuation of the test key. Finally, a back-up battery 18 may be provided, in order to assure continued operation in the event of failure of the principal power supply of the system.

Where appropriate, the supervision system can be supplemented by a remote alarm device comprising a shortrange high-frequency transmitter 19a connected to the electronic circuit 5 and a receiver 19b intended to be carried by a person responsible for the supervision of the perfusions. The receiver 19b may be equipped with an acoustic transducer for the emission of an audible alarm, as well as with display means permitting the identification of the perfusion set involved in an alarm.

The operation of the system will now be described, with reference to the algorithms of FIGS. 3 and 4, as well as to FIG. 5, which gives an example of the display on the visual display screen 14 for four perfusion sets.

Following the connection of the system to the power supply, the actuation of the RESET key 9 at the stage 20 leads to the stage 21 of initialization of the material part of the system and to the stage 22 of the display of waiting graphics on the visual display screen 14.

The following stage 23 is a test for the identification of the input key actuated by the operator. If the operator actuates the TEST key 8 (stage 24), the central unit implements a program 25 to monitor the number of perfusion sets P1 to Pn which are in service and displays a control code on the display device 17. When this test program 25 is completed, the procedure reverts to the stage 23.

If, following the test 23, the INITIALIZATION key 10 is actuated (stage 26), then the latter illuminates, as is the case for the actuation of the other keys, and the procedure passes to stage 27 of the execution of the initialization program.

The visual display screen is then subdivided into four vertical windows F1 to F4, in each of which the message "perfusion no." appears in flashing characters. The operator can then allocate to each window the number of one of the perfusion sets P to Pn to be supervised, by keying in the corresponding number on the digital keyboard 13 and by validating the instruction input in each instance by using the VALIDATION key 7. This number forms the identification code, which may adopt any other appropriate form, of the set to be supervised. The process is then carried out in sequences for the introduction of the data relating to the number of the room of the patient, to the perfusion liquid to be injected into him, to the volume of liquid to be perfused, and to the intended duration of perfusion. In the central unit there is stored a conversion table which, depending upon the nature of the liquid perfused and the number of drops which is measured per unit time, permits translation of this number of drops into a volume of liquid. When this sequence of operations has been completed, the initialization program causes the display, in the corresponding window of the screen 14, of a message indicating to the operator the average perfusion flowrate which is intended and reminding him to connect the perfusion set, the number of which is displayed in this window. If this connection has already been made, the corresponding item of data is supplied to the operator in the form of a reversal of the contrast of the windows initialized, as compared with the windows which have not been initialized.

The procedure then passes to the stage 28, in which a test on the connection of the perfusion sets is carried out. If this connection has not taken place, the procedure reverts to the initiation of test 28, while, in the opposite case, the operator is warned of this as indicated previously by a reversal of the contrast of the window corresponding to the set which has been initialized. The window of such a set then has the appearance shown for the second window F2 from the left in FIG. 5. This window includes, at its upper part, in the form of messages displayed in alphanumeric characters, the data relating to the perfusion set concerned, viz. the following: the number of the perfusion set, the number of the room of the patient, the nature of the perfusion liquid, the volume to be perfused V1, and the intended duration D1 of perfusion. On the other hand, the same window includes a graphical representation of a test-tube R, the width of which as shown is a function of the intended flowrate of liquid to be injected, the position of the level of which is a function of the remaining duration D of the perfusion, and the surface of which defined below this level is thus a function of the volume V of liquid remaining to be perfused. At the height of this level, there is also displayed an arrow, with which there are associated the letters V and D for identification of the two above indicated quantities and their numerical value expressed, for example, in cm$^3$ for the residual volume of liquid to be perfused and in minutes for the remaining duration. The window likewise includes a graphical representation G of a drip simulating, with a rhythm which is a function of the instantaneous flowrate measured, the actual fall of the drops taking place at the location of the container of the corresponding perfusion set. Finally, the window is completed by a linear volume unit meter VM, combining an analog representation of the instantaneous flowrate, as compared with authorized minimum and maximum values, with a digital display of these same values, the digital value of the instantaneous flowrate being adjacent to an arrow coinciding with the change of aspect of the two consecutive segments constituting the said analog representation.

When the response to the test 28 shows that the connection of the perfusion sets has actually been made, the procedure passes to the subprogram 30 for the management of the perfusion sets. This subprogram 30, the algorithm of which is represented in FIG. 4, is initialized on an interrupt 31. The interrupts may be generated by the central unit or by the perfusion sets themselves, according to an interrupt management protocol such as that described in French patent application FR-A-2,558,667, to which reference will be made. In the following text, it will be assumed that the interrupt originates from one of the modules M1 to Mn associated with the perfusion sets, the effect of which is to place the central unit in an interrogation condition to receive the message issued by this set (stage 32). The following stage 33 is a test carried out on the transmission effected between the perfusion set and the central unit. If this transmission is in default, an error message appearing on the display device 17 is issued in stage 34, after which the procedure reverts to stage 32. If the transmission is effected correctly, the central unit proceeds to the updating of the parameters intended to be displayed on the visual display screen 14, in the window to which is allocated the number corresponding to that of the perfusion set which has effected the transmission (stage 35). A test 36 is then carried out in order to verify whether the updated parameters correspond to a condition for the emission of an alarm. If this is the case, an alarm message is issued in stage 37.

The alarms which are issued may have the character of a simple warning or the character of urgency, and they will be designated in the following text as an amber alarm and a red alarm respectively. An amber alarm condition causes the flashing, on the screen 14, of the parameter concerned and possibly the illumination of a supplementary alarm warning light, and continues until the cessation of its cause, which may be:

a measured instantaneous flowrate which is outside of the minimum and maximum limits;

a zero instantaneous flowrate during a time less than a predetermined duration of, for example, 4 minutes, which is a function of the coagulation time of the blood;

a perfusion set which is disconnected during a time less than a predetermined duration of, for example, 4 minutes, which is a function of the coagulation time of the blood; and a red alarm situation converted into an amber alarm as a result of the pressing of the CLEAR key by the operator.

Red alarms are indicated by flashing of the parameter concerned on the visual display screen 14, flashing of the CLEAR key 11 and of the alarm warning light, where this is provided, the emission of an audible signal of the siren type or voice-synthesized message by the generator and the activation of the CLEAR key.

Moreover, if the system is equipped with the remote alarm system, the latter is activated in order to warn the nurse(s) responsible of the abnormal progress of the perfusion concerned. The nurse is notified by an audible signal of the existence of an anomaly and can identify on her portable receiver the set concerned, by virtue of the display means which indicate to her the number of the room of the patient or any other data item identifying the perfusion concerned.

A red alarm is triggered when the instantaneous flowrate remains zero or when a perfusion set remains unconneted for a period of time exceeding the above-mentioned predetermined duration, or, again, if the updating of the parameters indicates that the remaining duration of the perfusion is less than a predetermined value of, for example, 20 minutes.

The pressing of the CLEAR key 11 permits conversion of a red alarm into an amber alarm, that is to say interruption of the emission of the audible signal at the location of the generator 16 and the receiver 19b and cessation of the flashing of the warning light of the key. As a variant, this clearing function may be eliminated for safety reasons. The restoration of the system to a condition of conformity is obtained by eliminating the cause of the red alarm (zero flowrate or disconnected perfusion set), or by pressing one of the keys 10 and 12 for INITIALIZATION and for UPDATING, the warning lights of which are likewise illuminated in the course of the abovementioned end-of-perfusion period.

After stage 37 or, in the event of a negative response, after test 36, the procedure passes to the test 38 in order to determine whether the updated parameters correspond to a red alarm condition. If this is the case, a flag is triggered at 39 and the procedure then returns to the principal program (stage 40). The same applies if the response to the test 38 is negative.

The following stages 41 and 42 of the principal program consist in refreshing the base image and in updating the variable zones of this image, ie. the window of the perfusion set concerned. A test 43 is then carried out in order to determine whether one of the input keys 7 to 12 has been actuated. In the negative case, the procedure reverts to the commencement of the subprogram 30 for the management of the perfusion sets. This subprogram is repeated for each one of the perfusion sets with a repetition rate which is a function of the interrupts issued by the said sets, in such a manner that updating of the parameters of each one of the perfusion sets is assured with a period of, for example, one minute. In other words, each window of the visual display screen 14 is again updated every minute.

If the response to the test 43 is positive, this means that one of the keys 7 to 12 has been pressed in. The actuation of a key causes the issue of a particular code recognized by the central unit. If the key concerned is the CLEAR key 11 (stage 44), a test takes place at 45 in order to determine whether a flag has been triggered at the stage 39 of the subprogram 30. In the negative case, the procedure reverts to the test 43, while in the affirmative case a subprogram for conversion from a red alarm to an amber alarm is executed. After this subprogram 46, the procedure reverts to the commencement of the subprogram 30.

If the operator has operated the UPDATING key 12 (stage 47), the execution of an updating subprogram 48 takes place. This subprogram is similar to the initialization program and involves reupdating of the graphical representations in the windows only in circumstances in which the parameters which determine these representations have been modified. The end of this subprogram 48 leads back to the commencement of the subprogram 30.

In the event of the actuation of the TEST key (stage 49), the procedure passes to a test program 50 which is similar to that of stage 25, and then the proccedure reverts to the commencement of the subprogram 30.

Finally, operation of the INITIALIZATION key 10 leads back to the initialization program 27 (stage 51).

It will furthermore be noted that the sole function of the VALIDATION key 7 is to permit the central unit to accept the numerical values introduced by means of the keyboard 13 in the course of the initialization program 27 or of the updating program 48, and has no effect on the execution of the principal program in the other cases. Likewise, it will be noted that operation of the CLEAR key 11 or of the UPDATING key 12 in the course of the test 23 would directly lead back to the initiation of this test.

FIG. 6 shows a variant of the graphical representation appearing in a window of the visual display screen 14. In this variant, the container R has a symbolical shape of a perfusion bottle, and the volume unit meter VM is disposed vertically in the extension of what is supposed to be the orifice of this bottle. This volume unit meter VM is presented in the form of a series of consecutive elements of triangular shape 52 which symbolize drops. The end elements 52 corresponding respectively to the acceptable minimum flowrate and maximum flowrate, as well as the elements included between the minimum flowrate and the measured instantaneous flowrate, may have the same appearance, differing from that of the elements included between the measured instantaneous flowrate and the maximum authorized flowrate. As in the case of FIG. 5, numerical values may be displayed to represent the elements corresponding respectively to the minimum flowrate $\Delta$ min, to the maximum flowrate $\Delta$ max, to the measured instantaneous flowrate $\Delta$ instantaneous, and to the intended flowrate $\Delta$ intended.

It is likewise possible to use the volume unit meter VM of FIG. 6 to simulate the actual fall of the drops, with a rate which is a function of the measured instantaneous flowrate.

It is evident from the aforegoing statements that the system for remote supervision according to the invention permits the assurance of rigorous monitoring of the patients undergoing perfusion without the need for multiple visits to the patient's room. The progress of the perfusions may be supervised on a permanent basis, the conditions of supervision for the medical team are facilitated, and the time required in order to take action in the event of an anomaly is reduced to the shortest level. This system represents decisive progress for the monitoring of perfusions by gravity, while at the same time it can be adapted to other types of perfusion, in particular that carried out with the use of a programmed pump.

In order to take account of the conditions of hydrodynamic flow of the perfusions which are specific to each hospital department (type of tubing, height of the bottle in relation to the point of injection, ambient temperature, etc. . .), a graduated knurled knob situated at the rear of the central unit permits, on being operated manually, modification of the coefficient defining the basic unit volume of a drop (independently of any correction associated with the nature of the liquid or with the value of the flowrate). It is thus possible to calibrate the system as a function of the new practices adopted in the hospital department concerned (for example, a change in the suppliers of tubing).

In a preferred embodiment, the system described does not necessitate the setting-up of a supplementary connection infrastructure, by virtue of the utilization of the domestic low-tension electrical power distribution network. On the other hand, regardless of what movements a patient undergoing perfusion may undertake (change of bed, change of room), the patient remains under supervision, simply by connection to any wall socket. The perfusion set concerned continues to be identified by the number which is specific to it (identification code), and the data relating to this set are displayed on the window to which this number is allocated. If necessary, the operator will have to modify the room number appearing in the window. As a supplement to or in place of the room number, an identification code or the name of the patient may be displayed.

As a variant, it is possible to associate with each socket a subencoder to which the actual encoder will be connected. This subencoder will generate a geographic location code to supplement the identification code of the perfusion set, in such a manner that the identification of each set and its location will be undertaken automatically.

On the other hand, the application of a more extensive network, for example the switched network of the post and telecommunications authority, permits contemplation of telesupervision at home of the patients by means of this system. The latter is not limited as regards the number of perfusion sets to be monitored, the principal limitation concerning the capacity of the responsible person to supervise a large number of sets. By way of example, four visual display screens each divided into four vertical windows permit one and the same person to supervise up to sixteen perfusion sets.

Finally, it will be noted that this system may likewise be utilized for the remote control of perfusion sets by providing the module Muc with encoding capacity and the modules M1 to Mn with decoding capacity. For such remote control, it is likewise possible to rely on the network and on the protocol for the exchange of data between the peripherals and the central unit which are described in French Patent Application FR-A-2,558,667 which has already been mentioned. The central unit is then adapted to control each pump of a perfusion set as a function of reference values.

Moreover, it is possible to provide, for each perfusion container 1, a minimum level sensor formed, for example, by a photodiode associated with a phototransistor, and capable of detecting the change in the level of the liquid with reference to the change in the refractive index and of causing the triggering of the end-of-perfusion alarm.

We claim:

1. A monitoring system for the remote supervison of gravity perfusion sets, said monitoring system comprising:
   (a) a plurality of drip perfusion sets, each perfusion set including
      injecting means for injecting by gravity a liquid into a patient,
      measuring means for measuring the instantaneous flowrate of the liquid injected into a patient,
      encoding mdoule means for periodically generating a digital identification code specific to the corresponding perfusion set and a digital signal representing the instantaneous flowrate measured by the measuring means of said perfusion set,
   (b) a common data bus line to which each perfusion set to be supervised is connectable through its encoding module means at any one of a plurality of different geographical locations, and
   (c) a remote central monitoring unit including:
      data display means for displaying data pertaining to each perfusion set and data received from each perfusion set via said data bus line,
      decoding module means connected to said data bus line, and
      processor means operatively connected to said decoding module means and to said data display means for recognizing the identification code of each perfusion set connected to said data bus line, for converting each digital signal delivered by each perfusion set under supervison which is identified by its specific identification code to information representative of said measured instantaneous flowrate, and for displaying said information representative of the measured instantaneous flowrate in an area of said data display means allocated to each perfusion set in dependence of its identification code and independently of its geographical location along said data bus line.

2. The monitoring system as claimed in claim 1, wherein the remote central unit comprises a numeric keyboard means for entering the initial data of each perfusion to be monitored, including the volume of liquid to be injected, and wherein said processor means processes the instantaneous flowrate information in order to re-update periodically at least one of several quantities representing the condition of each perfusion in progress, including the remaining duration of the perfusion and the residual volume of liquid to be injected, and displays the updated quantities pertaining to each perfusion set on said allocated area of said display means.

3. The monitoring system as claimed in claim 2, wherein said central monitoring unit comprises an alarm generation means for the generation of alarms and wherein said processor means triggers said alarm generation means for generating (1) a first alarm in the event of detection of at least one of the following conditions:
   the instantaneous flowrate measured at a perfusion set is less than or greater than predetermined minimum and maximum values, respectively;
   the instantaneous flowrate measured at a perfusion set is zero; and
   a perfusion set is disconnected from the central monitoring unit;
and, (2) a second alarm in the event of detection of at least one of the following conditions:
   the instantaneous flowrate measured at a perfusion set remains zero for a period of time exceeding a first predetermined limit;
   a perfusion set is disconnected from the central monitoring unit for a period of time exceeding a second predetermined limit;
   the calcuated remaining duration of the perfusion at a perfusion set is less than a third predetermined limit.

4. The monitoring system as claimed in claim 3, wherein said central monitoring unit comprises a manually operable function key for controlling said alarm generation means so as to convert the second alarm into said first alarm upon triggering of said function key.

5. The monitoring system as claimed in claim 4, wherein said alarm generation means comprises light and audible signal emitting means for the illumination of at least one luminous warning light in response to the occurrence of one of said first alarm conditions and for the flashing of another warning light and the emission of an audible signal in response to the occurrence of one of said second alarm conditions.

6. The monitoring system as claimed in claim 2, wherein said central monitoring system comprises graphic generation circuit means connected to said processor means for displaying on each said allocated area of said data display means graphical symbolic representations of quantities representing the conditions of a specific perfusion set.

7. The monitoring system as claimed in claim 6, wherein said data display means comprise at least one monitoring screen onto which are displayed a plurality of vertical windows constituting said areas, each allocated for the display of the identification code of a specified perfusion set, information relating to the patient undergoing perfusion and said graphical symbolic representations of quantities representing the conditions of said specified perfusion set.

8. The monitoring system as claimed in claim 1, wherein said measuring means for measuring the instantaneous flowrate is a drop counter.

9. The monitoring system as claimed in claim 8, wherein a calibration means for the calibration of the unit volume of the drops counted by the drop counter is connected to the central unit.

10. The monitoring system as claimed in claim 1, wherein said common data bus line is a general-purpose transmission line of an electrical power distribution network.

11. The monitoring system as claimed in claim 1, wherein the injecting means of each perfusion set comprises a container including a level sensor adapted to supply a signal for the triggering of an alarm in response to the detection of a minimum level of liquid.

12. The monitoring system as claimed in claim 1, which comprises a remote alarm device comprising a high-frequency transmitter connected to the central unit and a portable receiver, said portable receiver exhibiting means for the generation of an alarm signal in the event of the detection of an anomaly of operation of a perfusion set by the central unit.

13. The monitoring system as claimed in claim 12, wherein said portable receiver comprises an acoustic transducer and means for the display of a data item identifying a perfusion set exhibiting an anomaly of operation.

* * * * *